United States Patent [19]
Yale

[11] Patent Number: 5,482,461
[45] Date of Patent: Jan. 9, 1996

[54] DISPOSABLE PROPHY ANGLE

[76] Inventor: Joyce K. Yale, 428 31st St., Hermosa Beach, Calif. 90254

[21] Appl. No.: 426,632

[22] Filed: Apr. 21, 1995

Related U.S. Application Data

[63] Continuation of Ser. No. 250,528, Mar. 31, 1994, abandoned.

[51] Int. Cl.⁶ ..................................................... A61C 3/06
[52] U.S. Cl. ........................................... 433/125; 433/166
[58] Field of Search ..................................... 433/115, 125, 433/126, 134, 166

[56] References Cited

U.S. PATENT DOCUMENTS

| | | | |
|---|---|---|---|
| 952,437 | 3/1910 | Miller | 433/134 |
| 1,499,346 | 7/1924 | Chott | 433/134 |
| 1,837,938 | 12/1931 | Young | 433/166 |
| 2,451,918 | 10/1948 | Chott | 433/166 |
| 3,599,333 | 8/1971 | Muhler | 433/166 |
| 3,727,313 | 4/1973 | Graham | 433/125 |
| 3,798,777 | 3/1974 | Reiter | 433/125 |
| 4,182,041 | 1/1980 | Girard | 433/125 X |
| 4,636,171 | 1/1987 | Martin | 433/134 |
| 5,028,233 | 7/1991 | Witherby | 433/125 |
| 5,120,220 | 6/1992 | Butter | 433/125 |
| 5,209,658 | 5/1993 | Brahler . | |

*Primary Examiner*—Nicholas D. Lucchesi
*Attorney, Agent, or Firm*—Poms, Smith, Lande & Rose

[57] ABSTRACT

A dental prophylaxis angle of the snap-on variety comprising two interlocking external parts and 2 internal parts, wherein the base for the mandrel or button formation resembling a knob which arises from the rotary bearing, known as a slinger ring or disk or annular stop, designed to receive the conventional snap-on rubber-like prophylaxis cup, has a plurality of sharp pointed projections or prongs to safely grip and stabilize the engagement of a snap-on prophylaxis cup.

10 Claims, 1 Drawing Sheet

DISPOSABLE PROPHY ANGLE

This application is a continuation of now abandoned application, Ser. No. 08/250,528, filed May 31, 1994.

BACKGROUND OF THE INVENTION

The receiving button or knob on the traditional snap-on prophylaxis angle, whether metal or disposable plastic, has the failing of allowing the rubber snap-on prophylaxis cup to slip or slide upon that knob and base when that knob and base are rotating in an attempt to polish the teeth. When the cup and its pumice are placed on the tooth surface, only the attachment knob or button of the mandrel, upon which the prophylaxis cup is placed, moves; the rubber prophylaxis cup does not. There can be no polishing without prophylaxis cup movement.

All of the existing prophylaxis right angles of the snap-on prophy cup style are basically useless. This style is most common with the disposable prophy angles which are not used by dental hygienists due to the slipping of the rubber snap-on prophy cup as it rides upon the smooth knob. Disposable prophy angles are desirable due to patients' fear of sterilization procedures within the dental office. With prongs arising not from the prophylaxis angle mandrel's knob, but from the base or slinger ring, the rubber snap-on prophylaxis cup will be securely gripped and will rotate with the same revolutions as the mandrel's knob, or button in a safe manner which means the projections will not ever be able to laterally puncture the rubber of the praphy cup and thereby lacerating the gum tissue. The prongs will prevent spinning of the knob within the affixed rubber prophylaxis cup's base cavity and force it to rotate with the rotation of the rotor as expected.

The improvement of the attachment device on this prophylaxis angle will allow the operator to use a snap-on style prophylaxis angle in the desired manner.

This invention is an improvement on the dental prophylaxis right angle which receives the rubber prophy cup referred to as a snap-on style. The constant problem with the conventional snap-on prophylaxis right angle is that the prophy cup will not consistently rotate with the rotation of the knob on the prophylaxis right angle because the knob is a smooth structure which fails to grip the snap-on rubber prophy cup, and therefore spins independently within the affixed rubber prophy cup at the time the prophy cup is placed in contact with the tooth with slight pressure in order to cause the tooth to be polished. This is unfortunate as the snap-on disposable prophylaxis right angle is very desirable. Also, the snap-on disposable prophylaxis right angle is more economical to make than the type which receives the screw-on prophy cup which will not slip during the procedure.

DESCRIPTION OF THE PRIOR ART

U.S. Pat. No. 5,120,220 (D. Butler Jun. 09, 1992) is a Right Angled Dental Hand Piece which has a smooth knob (41) and slinger disk (36) and no other means of attaching and securing a snap-on prophy cup.

U.S. Pat. No. 5,040,978 (C. J. Falcon, Aug. 20, 1991) is a Dental Prophy Angle which includes a "prophy cup rotation member" (15), which is smooth as is the slinger disk.

U.S. Pat. No. 5,028,233 (K. Witherby, Jul. 02, 1991) is a Disposable Prophy Angle which includes "a mandrel or button formation of conventional shape" (21), which is smooth as is the slinger disk.

U.S. Pat. No. 5,020,994 (J. T, Huang, Jun. 04, 1991) is a Disposable Prophylaxis Angle which does not mention a knob or button, but which indeed is manufactured with the smooth knob and slinger disk.

U.S. Pat. No. 4,182,041 (H. W. Girard Jan. 08, 1980) is a Dental Prophylactic Right Angle Hand Piece which includes a "serrated knob" (72), which will not grip sufficiently the rubber of the snap-on prophy cup to prevent its slipping as the knob rotates with the customary speed provided by the operating hand piece. This is the only prior art which addresses the slipping of the rubber prophy cup as it rides upon the knob or button, however it is insufficient in its gripping ability. To lengthen the serrated points would increase the danger of passing through the rubber prophy cup and risk cutting the patient's tissue with said serrations as the teeth are being polished with the rubber prophy cup. The slinger disk upon which sits the knob is smooth.

U.S. Pat. No. 3,869,877 (G. R. Brahler Mar. 11, 1975) is a Drive Shaft which includes a "button (24) over which the workpiece may be readily snap-fitted" which is smooth as is the slinger disk.

U.S. Pat. No. 3,798,777 (G. Reiter Mar. 26, 1974) is a Dental Handpiece which includes a "head (52) for removable snap-on engagement of prophy cups" which is smooth as is the slinger disk.

U.S. Pat. No. 3,740,853 (G. R. Brahler Jun. 26, 1973)is a Dental Prophy Angle which includes a "button" (54) which is smooth as is the slinger disk.

U.S. Pat. No. 3,727,313 (R.C. Graham Apr. 17, 1973) is a Dental Prophylaxis Right Angle Hand Piece which includes a "knob or enlargement" (21) which is smooth as is the slinger disk.

U.S. Pat. No. 3,163,934 (A. D. Wiseman Jan. 05, 1965) is a Dental Prophylaxis Right Angle Hand Piece which has a "bulbous end" (28) which is smooth as is the slinger disk.

SUMMARY OF THE INVENTION

The present invention is an improvement of the traditional prophylaxis angle, whether it is made of metal (sterilizable) or plastic (single use or disposable), which utilizes the rubber snap-on prophy cup or other snap-on tools.

The present invention is made of four parts, two are the hollow external parts which snap together with lateral locking devices, and two are the internal works comprised of two integrating gear members. One of these gear members has an elongated spindle or drive shaft which passes beyond the lower opening of the prophylaxis angle which attaches to the dental handpiece. At the other end of the prophylaxis angle, the other internal gear member has a protruding knob or button upon which the snap-on prophy cup sits. The base of the prophy cup is pierced and thus anchored by the projections arising from the slinger disk, or base of the button, which is one end of the driven gear rotor.

The inefficiency of the current snap-on prophy angle is seen when the operator positions the prophy cup on the tooth and steps on the handpiece engine's accelerator. Every part of the prophy angle moves except the rubber snap-on prophy cup because as in the prior art there has been no means by which it can be firmly and securely attached to the knob or button area which receives the rubber prophy cup. Instead, the knob spins freely within the cavity of the snap-on prophy cup.

According to this invention, the prophylaxis angle is provided with a means of secure attachment of the rubber prophy cup in the form of small sharp pointed projections arising from the base of the knob which is known as the slinger disk. These projections pierce the rubber base of the snap-on prophy cup and force it to rotate at the same speed the knob is rotating, thus eliminating the free spinning of the knob within the cavity of the snap-on prophy cup.

The object of this invention is to provide the operator a prophy angle which will work as it is intended to work without the frustrating spinning of the receiving knob and the slipping of the rubber prophy cup as it sits on that knob.

A further object of this invention is to provide the operator with a disposable plastic prophy angle which will actually work and insure patient safety.

The novel feature which is believed to be characteristic of this invention are the sharp pointed projections arising from the slinger disk or base of the attachment knob of the prophy angle.

These objects and advantages of this invention will become apparent upon reading the following description of which the attached drawings form a part.

DESCRIPTION OF THE PREFERRED EMBODIMENT

Figure 1:
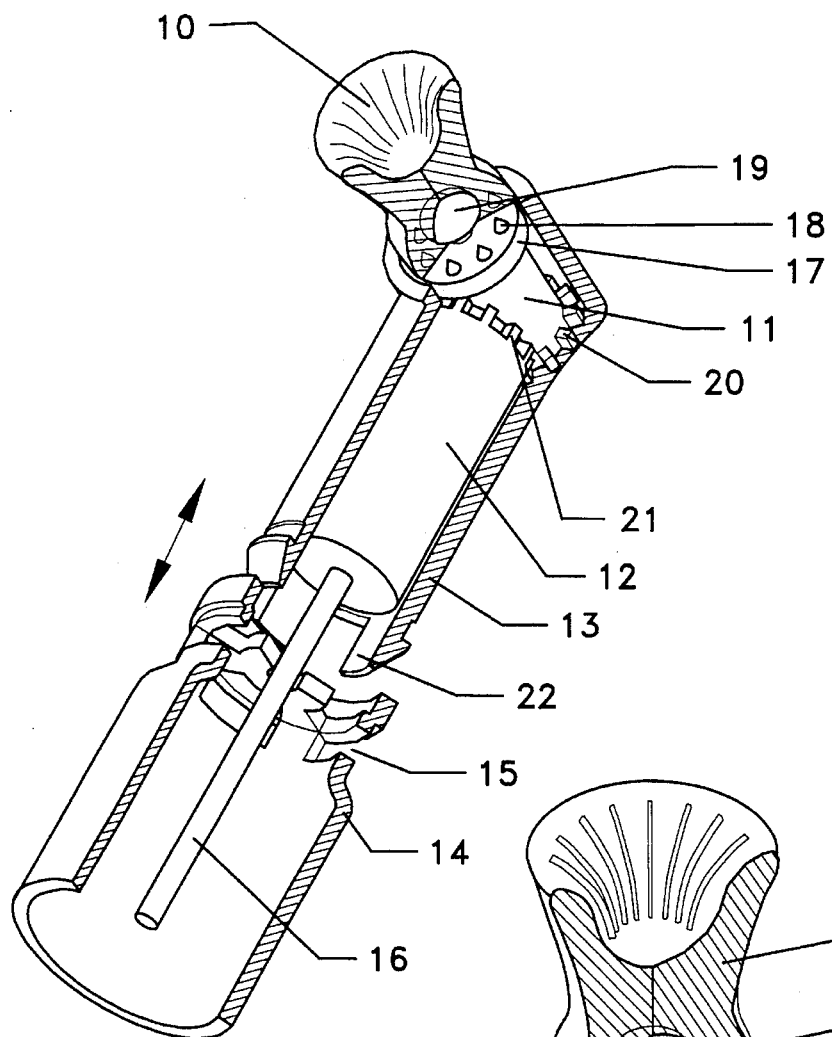
FIG. 1 is an enlarged sectional view of the dental prophylaxis right angle in accordance with the present invention with a prophy cup in place.

FIG. 1 shows a sectional view of the present invention which consists of a tubular housing in two intersecting sections (13) and (14) securing with a latch (22) on an upper portion (13) into a cavity (15) on a lower portion (14). The upper portion (13) receives a rotor (11) formed on a driven gear (20), with a prophy cup attached (10) and pierced by a plurality of sharp pointed projections (18) arranged circumferentially arising from a slinger disk (17) surrounding an attachment knob (19) or mandrel extension at an external end of the rotor (11), and the rotor (12) having a driving gear formed thereon (21) which comprises the upper portion of an elongated driving shaft or spindle (16) where a conventional dental handpiece attaches thereto.

Figure 2:
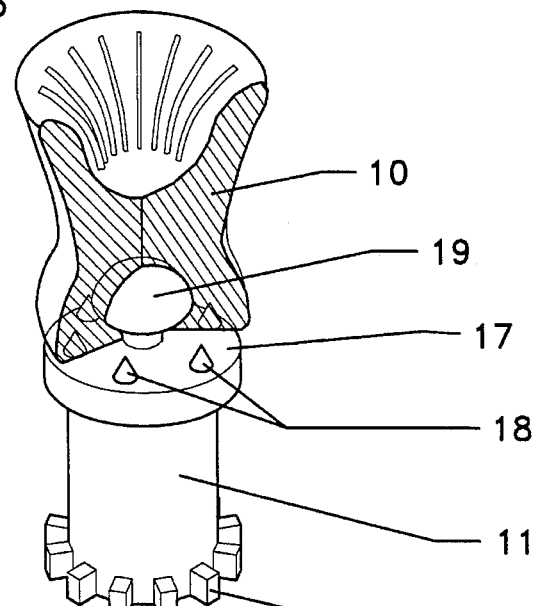
FIG. 2 is an enlarged view of the driven rotor of the prophylaxis right angle with a prophy cup attached to the knob of the slinger disk, showing the sharp projections piercing a snap-on prophy cup at its base.

FIG. 2 in a larger scale perspective, shows a driven rotor (11) and gear (20) with the slinger disk (17) extension which has sharp pointed projections (18) arranged circumferentially upon the slinger disk (17) to secure a snap-on prophy cup (10) as it rides upon a knob (19) or mandrel projection. These sharp pointed projections (18) are shown piercing the base of the snap-on prophy cup (10).

Figure 3:
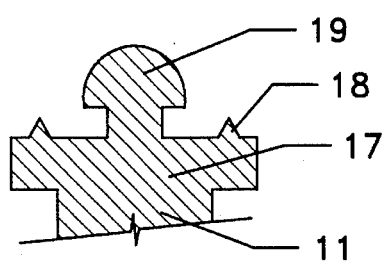
FIG. 3 is an enlarged cross section view of the upper portion of the driven rotor showing the knob and sharp projections upon the slinger disk as it extends from the driven rotor.

FIG. 3 shows a cross section of the upper portion of the driven rotor (11) with the slinger disk (17) extension upon which the sharp projections (18) are arranged circumferentially around the knob (19).

I claim:

1. A prophylaxis right angle comprising an outer body and an inner body having therein a rotor of a driving gear which interacts with a rotor of a driven gear having a slinger disk an attachment knob on said slinger disk, said slinger disk having a center, said slinger disk including a plurality of raised projections extending from the surface of the slinger disk to engage the base portion of a prophy cup when the base opening of a prophy cup receives the attachment knob to cause a prophy cup to rotate with the same rotation of the attachment knob, said raised projections being spaced a distance from said center of said slinger disk.

2. The improvement of claim 1 wherein each of said projections has a sharp point to pierce the base portion of a prophy cup.

3. The improvement of claim 1 wherein the projections are arranged circumferentially about the peripheral edge region of the attachment knob.

4. A prophylaxis right angle, comprising a driven gear having a rotor, a slinger disk, said slinger disk located on the rotor and an attachment knob extending from the slinger disk, having a surface surrounding the attachment knob and at least one raised pointed projection extending from the surface of the slinger disk to pierce and engage a prophy cup having a base portion with a base opening adapted to receive said attachment knob so as to ensure rotation of the prophy cup with rotation of the attachment knob.

5. The prophylaxis right angle of claim 4 wherein a plurality of projections are provided to extend from the surface of the slinger disk.

6. The prophylaxis right angle of claim 4 wherein a plurality of projections are provided and are arranged circumferentially on the slinger disk base of the attachment knob, said slinger disk having a center, said projections being spaced from said center.

7. A prophylaxis right angle as defined in claim 4, wherein said slinger disk has a center, said at least one projection being spaced from said center.

8. A prophylaxis right angle comprising:

an outer housing;

an inner mechanism that is substantially within said outer housing, said inner mechanism comprising a rotatable slinger disk connected to a rotor, said slinger disk having a peripheral edge region and a center;

a plurality of pointed projections arranged substantially circumferentially about and extending from said peripheral edge region of said slinger disk, said pointed projections being spaced a distance from said center of said slinger disk; and a removable prophy cup mounted on said pointed projections, said prophy cup having an outer portion and a base;

wherein said pointed projections serve to prevent said outer portion of said base of said prophy cup from substantially rotating relative to said slinger disk.

9. A prophylaxis right angle as defined in claim 8, wherein said plurality of pointed projections comprises at least six projections.

10. A prophylaxis right angle as defined in claim 8, wherein said inner mechanism further comprises a knob mounted on said slinger disk at said center of said slinger disk, said prophy cup being removably mounted on said knob and on said pointed projections, said pointed projections being spaced a distance from said knob.

\* \* \* \* \*